United States Patent [19]

Peyman et al.

[11] Patent Number: 5,278,152
[45] Date of Patent: Jan. 11, 1994

[54] 2-FORMYLBENZYLPHOSPHONIC ACID DERIVATIVES USEFUL FOR THE TREATMENT OF DISEASES CAUSED BY VIRUSES

[75] Inventors: Anuschirwan Peyman, Kelkheim; Eugen Uhlmann, Glashütten; Irvin Winkler, Liederbach; Matthias Helsberg, Kelkheim; Christoph Meichsner, Hofheim am Taunus, all of Fed. Rep. of Germany

[73] Assignee: Hoechst Aktiengesellschaft, Frankfurt am Main, Fed. Rep. of Germany

[21] Appl. No.: 19,822

[22] Filed: Feb. 18, 1993

Related U.S. Application Data

[63] Continuation of Ser. No. 920,532, Jul. 28, 1992, abandoned, which is a continuation of Ser. No. 603,514, Oct. 26, 1990, abandoned.

[30] Foreign Application Priority Data

Dec. 21, 1989 [DE] Fed. Rep. of Germany ....... 3942318

[51] Int. Cl.$^5$ ................. A61K 31/685; A61K 31/66; C07F 9/40; C07F 9/38
[52] U.S. Cl. ........................ 514/76; 514/89; 514/92; 514/125; 514/101; 546/22; 548/119; 558/190; 558/198; 549/221
[58] Field of Search ............ 514/76, 89, 92, 125; 546/22; 548/119; 558/190, 198

[56] References Cited

U.S. PATENT DOCUMENTS

| | | | |
|---|---|---|---|
| 3,953,546 | 4/1976 | Hirano et al. | 558/190 |
| 4,217,346 | 8/1980 | Diana | 514/119 |
| 4,299,615 | 11/1981 | Gourse | 504/207 |
| 4,436,736 | 3/1984 | Hodakawski et al. | 558/190 |

FOREIGN PATENT DOCUMENTS

| | | | |
|---|---|---|---|
| 0313002 | 4/1989 | European Pat. Off. | |
| 0594123 | 2/1978 | U.S.S.R. | 558/198 |

OTHER PUBLICATIONS

Gardner, M. B., & Luciw, P. A., "Animal Models of AIDS," FASEB J. vol. 3, 1989, pp. 2593-2606.
Kosolapoff, G. M. Organophosphorus Compounds; John Wiley and sons: New York, 1950; pp. 121-123.
Morrison, R. T. et al. Organic Chemistry; 4th ed.; Allyn and Bacon: Boston, 1983; pp. 756-758.
Greene, T. W. Protective Groups in Organic Synthesis; John Wiley and Sons: New York, 1981; pp. 122, 124, 144, 147.

*Primary Examiner*—Robert W. Ramsuer
*Assistant Examiner*—Michael G. Ambrose
*Attorney, Agent, or Firm*—Finnegan, Henderson, Farabow, Garrett & Dunner

[57] ABSTRACT

The compound of the formula I

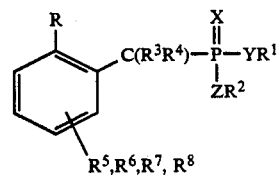

in which R is an aldehyde group or a group which can be converted into an aldehyde, $R^1$ and $R^2$ are alkyl, alkenyl, alkynyl, aralkyl, cycloalkyl, hydrogen, sodium, potassium, calcium, magnesium, aluminum, lithium, ammonium or triethylamnonium, or $R^1$ and $R^2$ together form a cyclic diester,
$R^3$ and $R^4$ are alkyl, alkenyl, alkynyl, cycloalkyl, hydrogen, alkoxy or halogen, $R^5$ and $R^8$ are alkyl, alkenyl, alkynyl, aralkyl, cycloalkyl, alkoxy, phenyl, cyanide, hydroxyl or hydrogen, and X, Y or Z are oxygen or sulfur, or prodrug forms of the compound of the formula I can be used for the treatment of diseases caused by viruses.

The preparation of these compounds and pharmaceutical preparations containing them and their use is described.

8 Claims, No Drawings

2-FORMYLBENZYLPHOSPHONIC ACID DERIVATIVES USEFUL FOR THE TREATMENT OF DISEASES CAUSED BY VIRUSES

This application is a continuation of application Ser. No. 07/920,532, filed Jul. 28, 1992, now abandoned, which is a continuation of Ser. No. 07/603,514, filed Oct. 26, 1990, abandoned.

DESCRIPTION

The invention relates to novel 2-formylbenzylphosphonic acid derivatives, to processes for the preparation of these compounds, to pharmaceutical agents which contain the active compounds according to the invention and to their use as medicoments, in particular for the treatment of diseases caused by viruses.

In order to treat diseases caused by viruses, various preparations have hitherto been employed, such as, for example, nucleoside analogs, amantadine, pyrophosphate analogs or imnunomodulators (M. J. Wood, A. M. Geddes, The Lancet, 1987, 1189). Some phosphonic acid derivatives are known which exhibit antiviral activity. These include compounds such as phosphonoformic acid (PFA), phosphonoacetic acid (PAA), methylenediphosphonic acid (MDP) and tetrazolephosphonic acids (S. M. Roberts, NATO ASI Ser., Ser. A 143, 1988, 37; D. W. Hutchinson, M. Naylor, Nucleic Acids Res., 13, 1985, 8519). PFA has a wide antiviral spectrum, but causes some toxic side effects, which have hitherto prevented development to the antiviral medicament (M. J. Wood, A. M. Geddes, The Lancet, 1987, 1189). It is known of ortho-phosphonyloxyacetophenone derivatives that they are especially active against picornaviruses (EP 21,000).

Diana et al. (J. Med. Chem. 27, 1984, 691; DOS 2,922,054) report on a class of compound of the type

in which A is an aromatic ring and C is a phosphonate or a β-ketophosphonate in which A and C are separated from one another by means of a bridge of 3–8 methylene groups (B). From this class of compound, arylalkylphosphonic acids having methylene bridges of more than 5 carbon atoms showed antiviral activity against herpesviruses. However, arylalkylphosphonic acids having methylene bridges of less than 5 carbon atoms do not show antiviral activity. The substitution of the aromatic radical of these compounds is carried out, in Diana et al., essentially by means of a 2-chloro-, 4-methoxyor 4-carbethoxyphenoxy group.

Benzylphosphonic acids have hitherto not been described as active antiviral compounds (J. C. H. Mao et al., Anti-microb. Agents Chemother. 27, 1985, 197).

Surprisingly, it has now been found that 2-formylbenzylphosphonic acid derivatives have antiviral activity.

The invention therefore relates to a compound of the formula I

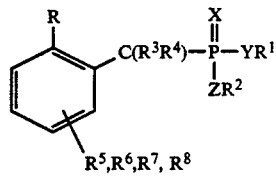

in which
R is an aldehyde group or a group which can be converted into an aldehyde,
$R^1$ and $R^2$ which may be the same or different, are a straight-chain or branched alkyl group having 1 to 20 carbon atoms a straight-chain or branched alkeryl or alkynyl group having 2 to 20 carbon atoms, an aralkyl group having 7 to 20 carbon atoms, a cycloalkyl group having 3 to 8 carbon atoms, hydrogen, sodium, potassium, calcium, magnesium, aluminum, lithium, ammonium or triethylammonium or $R^1$ and $R^2$ together form a cyclic diester having 2 to 6 carbon atoms in the ring, $R^3$ and $R^4$, which may be the same or different, are a straight-chain or branched alkyl group having 1 to 20 carbon atoms, a straight-chain or branched alkynyl or alkenyl group having 2 to 20 carbon atoms, a cycloalkyl group having 3 to 8 carbon atoms, an alkoxy group having 1 to 4 carbon atoms, hydrogen, fluorine, chlorine, bromine or iodine,
$R^5$, $R^6$, $R^7$ and $R^8$, which may be identical or different, are a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, an alkoxy group having 1 to 4 carbon atoms, hydrogen, fluorine, chlorine, bromine, iodine, a cyanide, hydroxyl or phenyl group or the radical of the formula Ia

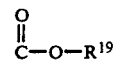

$R^{19}$ is a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, hydrogen, sodium, potassium, calcium, magnesium, aluminum, lithium, amonium or triethylammonium and
X, Y and Z, which may be identical or different, are oxygen or sulfur or a prodrug form of the compound of the formula I.
A compound of the formula I in which
$R^1$ and $R^2$ are an alkyl group having 1 to 10 carbon atoms, an alkenyl or alkynyl group having 2 to 10 carbon atoms, hydrogen or an aralkyl group having 7 to 16 carbon atoms,
$R^3$ and $R^4$ are an alkyl group having 1 to 4 carbon atoms, an alkenyl or alkynyl group having 2 to 4 carbon atoms or hydrogen,
$R^5$, $R^6$, $R^7$ and $R^8$ are chlorine, bromine, methoxy or hydrogen and
X, Y and Z are oxygen, is preferred.
By the term "prodrug form of the compound of the formula I", compounds are meant which are converted into a compound of the formula I in which R is an aldehyde group, en route to the site of action. In the article by H. Bundgaard (Design of Prodrugs, 1985, pp. 1-92, Elsevier-Verlag), the term "Prodrug form" is defined and illustrated by examples.

The notation alkyl group having 1 to 10 carbon atoms is to be understood as meaning, for example, the following radicals: methyl, ethyl, propyl, isopropyl, n-butyl, sec.-butyl, tert.-butyl, 2,2-dimethyl-1-propyl, n-pentyl, n-hexyl, n-heptyl, n-octyl, n-nonyl and n-decyl. By the notation alkenyl group having 2 to 10 carbon atoms, the following compounds, for example, are meant: ethenyl, propenyl, butenyl, pentenyl, hexenyl, heptenyl, octenyl, nonenyl or decenyl. By the notation alkynyl group having 2 to 10 carbon atoms, the following compounds are meant, for example: ethynyl, propynyl, butynyl, pentynyl, hexynyl, heptynyl, nonynyl, octynyl or decynyl. An aralkyl group having 7 to 16 carbon atoms is understood as meaning the following radicals, for example: phenylmethyl, phenylethyl, phenylbutyl, phenylpropyl, phenylpentyl, phenylhexyl, phenylheptyl, phenyloctyl, phenylnonyl or phenyldecyl. A cycloalkyl group having 3 to 8 carbon atoms is understood as meaning radicals such as cyclopropyl, cyclobutyl, cyclopentyl, cyclohexyl, cycloheptyl or cyclooctyl. Alkoxy groups having 1 to 4 carbon atoms are radicals such as methoxy, ethoxy, propoxy, isopropoxy, n-butoxy, sec.-butoxy or tert.-butoxy.

The invention furthermore relates to a process for the preparation of the compound of the formula I in which R is an aldehyde group, which comprises reacting the compound of the formula II

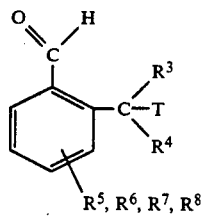

II in which

R$^3$ and R$^4$ which may be the same or different, are a straight-chain or branched alkyl group having 1 to 20 carbon atoms, a straight-chain or branched alkynyl or alkenyl group having 2 to 20 carbon atoms, a cycloalkyl group having 3 to 8 carbon atoms, an alkoxy group having 1 to 4 carbon atoms, hydrogen, fluorine, chlorine, bromine or iodine, R$^5$, R$^6$, R$^7$ and R$^8$, which may be identical or different, are a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, an alkoxy group having 1 to 4 carbon atoms, hydrogen, fluorine, chlorine, bromine, iodine, a cyanide, hydroxyl or phenyl group or the radical of the formula Ia

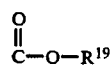

Ia

R$^{19}$ is a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, hydrogen, sodium, potassium, calcium, magnesium, aluminum, lithium, ammonium or triethylammonium and T is chlorine, bromine, iodine, methylsulfonate, phenylsulfonate or tosylsulfonate, with the compound of the formula III

III in which,

R$^1$ and R$^2$, which may be the same or different, are a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, hydrogen, sodium, potassium, calcium, magnesium, aluminum, lithium, ammonium or triethylammonium or R$^1$ and R$^2$ together form a cyclic diester having 2 to 6 carbon atoms in the ring, R$^9$ is a straight-chain or branched alkyl group having 1 to 4 carbon atoms and X, Y and Z, which may be identical or different, are oxygen or sulfur.

The invention furthermore relates to a process for the preparation of the compound of the formula I in which R is a group which can be converted into an aldehyde, which comprises reacting the compound of the formula I in which R is an aldehyde in such a way that a group which can be converted into an aldehyde is formed.

The term "group which can be converted into an aldehyde" is understood as meaning radicals which are converted into an aldehyde en route to the site of action (H. Bundgaard, Design of Prodrugs, 1985, pp. 1-92, Elsevier-Verlag).

In particular, the aldehyde group can be derivatized in such a way that the compound of the formula I is formed in which R is a group, which can be converted into an aldehyde, of the formula Ib, Ic or Id

Ib

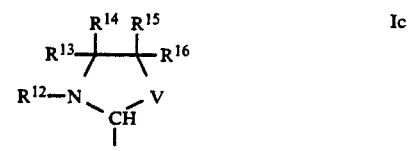

Ic

Id in which R$^{10}$ and R$^{11}$, which may be identical or different, are a straight-chain or branched alkyl group having 1 to 10 carbon atoms or R$^{10}$ and R" together form a cyclic acetal having 2 or 3 carbon atoms in the ring, R$^{12}$ to R$^{16}$, which may be identical or different, are a straight-chain or branched alkyl group having 1 to 10 carbon atoms or an aryl group having 6, 10 or 14 carbon atoms, V is oxygen or sulfur, M is a hydroxyl group, a straight-chain or branched alkyl group having 1 to 10 carbon atoms, an aralkyl group having 7 to 20 carbon atoms, an aryl group having 6, 10 or 14 carbon atoms or a radical of the formula Ie or If

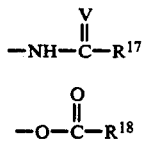

in which $R^{17}$ is a straight-chain or branched alkyl group having 1 to 10 carbon atoms, an amino, pyridine, or an aryl group having 6, 10 or 14 carbon atoms and $R^{18}$ is an amino group, a pyridine group, a straight-chain or branched alkyl group having 1 to 10 carbon atoms, an aryl group having 6, 10 or 14 carbon atoms or an aralkyl group having 7 to 20 carbon atoms.

The synthesis of the compound of the formula I in which R is an aldehyde group is carried out by reacting the compound of the formula II with the compound of the formula III, expediently at temperatures between 100 and 250° C., preferably between 120° and 180° C. (U.S. Pat. No. 4,299,615; Houben-Weyl, Methoden der Org. Chemie (Methods of Organic Chemistry), vol. XII/1, page 423, Thieme-Verlag, Stuttgart; Houben-Weyl, Methoden der Org. Chemie (Methods of Organic Chemistry), Vol. E2, page 300). The reaction can be carried out in a suitable solvent, such as hexamethylphosphoramide (HMPA), dimethylylformamide (DMF), dimethyl sulfoxide (DMSO), N,N'-dimethyl-N,N'-propyleneurea (DMPU) or NN'-dimethyl-N,N'-ethyleneurea (DMEU). The reaction can also be carried out without solvent. Purification is carried out by generally customary methods, preferably by chromatography on silica gel using suitable eluents, by distillation or by recrystallization from suitable solvents.

The compounds of the formula II and III can be prepared in a manner known per se. The conversion of the phosphonic acid diesters into their monoesters, and also into the corresponding free acids or their salts is carried out, for example, by boiling with dilute hydrochloric acid (Houben-Weyl, Methoden der Organischen Chemie (Methods of Organic Chemistry), Vol. XII/1, 1963), or by reaction with trimethylbromosilane (C. E. McKenna, J. Schmidhauser, J. C. S. Chem. Commun., 1979, 739). Purification is carried out by recrystallization in suitable solvents or by chromatographic methods, preferably by ion exchange chromatography using suitable eluents. The desired salt forms can also be obtained by ion exchange chromatography.

The synthesis of a prodrug form of the compound of the formula I can be carried out, for example, by derivatizing the aldehyde group in the compound of the formula I in such a way that compounds such as oximes, thiosemicarbazones, carboxylic acid hydrazones, Schiff's bases, oxazolidines, thiazolidines or acetals are formed. For this purpose, the compound of the formula I in which R is an aldehyde group can be reacted with the compound of the formula IVa, IVb and/or IVc, IVd or IVe

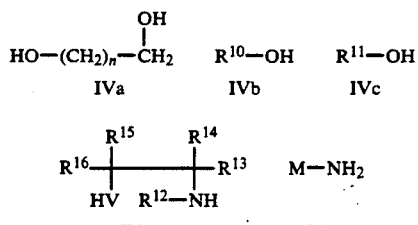

in which $R^{10}$ to $R^{16}$, M and V have the meaning mentioned and n is 1 or 2.

Other prodrug forms are formed in an analogous manner by the methods described in Bundgaard. The compounds of the formula I derivatized on the aldehyde group can be converted in vitro and in vivo into the active, antivirally active form (aldehyde form) (H. Bundgaard, Design of Prodrugs, 1985, 1–92, Elsevier-Verlag). The conversion into the active form can be carried out, for example, by hydrolysis in aqueous solution or by enzymatic catalysis in or en route to the site of action.

A test for activity of chemotherapeutics for HIV infections in man causes difficulties, since no infection model in laboratory animals yet exists. Infection with other retroviruses therefore has to be resorted to for testing chemotherapeutics. In this case, the infection of the mouse with the Friend leukemia virus has been chosen. For this purpose, normal NMRI laboratory mice (NMRI=Naval Medical Research Institute) were infected by intravenous injection with mouse serum containing Friend leukemia virus. In the untreated control animals, a distinct enlargement of the spleen and liver developed as a symptom of the infection in the course of 2 weeks. Treatment was carried out over 10 days, starting 48 hours after the infection. On the 14th day of the experiment, the animals were sacrificed and dissected. The spleen was removed and weighed. As a measurement parameter of the therapeutic activity, the weight of the spleen of the treated animals was related to that of the untreated infection control.

In the case of uninfected adult laboratory mice (20–24 g body weight), the spleen weighed about 1% of the body weight or less, while in the case of infected animals, the spleen attained about 10% of the body weight at the end of the experiment.

The compound of the formula I in which R is an aldehyde group possesses useful pharmacological properties, in particular an antiviral action and in particular against diseases caused both by DNA and RNA viruses, particularly against diseases which are caused by Herpes simplex virus (HSV I), myxoviruses, Friend leukemia virus (FLV) or human immunodeficiency virus (HIV). The compounds according to the invention are therefore suitable for combating various diseases caused by viruses, such as respiratory tract disease, diseases of the skin, the eyes, the central nervous system, AIDS and AIDS-related conditions, such as AIDS-related complex (ARC), generalized lymphadenopathy (GL), AIDS-related neuralgic conditions (such as mental deficiency or trophic paraparesis), anti-HIVantibody-positive conditions, Kaposi sarcoma or thrombopenic purpura.

The compound of the formula I and/or its prodrug form can either be used as a pharmaceutical alone or mixed with physiologically tolerable auxiliaries or excipients in effective amounts. It can be administered, for example, orally in a dose of 1 to 500 mg/kg/day, preferably 5 to 50 mg/kg/day. The administration for parenteral, rectal or topical use or as an aerosol is carried out, for example in an amount of 0.5 to 500 mg/kg/day, preferably of 2 to 100 mg/kg/day. The compound of the formula I and/or its prodrug form are expediently administered in dosage units which contain at least the effective amount of the compounds according to the invention, preferably 25 to 6000 mg, particularly preferably 100 to 1000 mg. These values relate to an adult human having a weight of 75 kg. These dosage units can also be administered several times per day. The dosage can also be increased in severe cases. In many cases, however, lower amounts are also sufficient. For combating diseases which are caused by RNA or DNA viruses, the following are suitable in particular diethyl 2-formylbenzylphosphonate, 2-formylbenzylphosphonic acid di(triethylammonium) salt, monoethyl 2-formylbenzylphosphonate triethylammonium salt, diethyl 2-formylbenzylphosphonate thiosemicarbazone, diethyl 2-formylbenzylphosphonate nicotinic acid hydrazone or diethyl 2-(3,4-dimethyl-5-phenyloxazolidin-2-yl)benzylphosphonate.

The compound of the formula I according to the invention and/or its prodrug form can also be administered in combination with other substances, in particular antiviral agents and immunostimulators, such as interferons.

The compound of the formula I and/or its prodrug form are referred to as the active compound in the following.

The invention furthermore includes the use of the active compound in the preparation of pharmaceuticals which are employed for the treatment and prophylaxis of the above-mentioned diseases. The invention furthermore relates to pharmaceuticals which contain one or more active compounds.

The pharmaceuticals are prepared by processes which are known per se and familiar to those skilled in the art. As a pharmaceutical, the active compound is either employed as such or preferably in combination with suitable pharmaceutical auxiliaries or excipients in the form of tablets, coated tablets, capsules, suppositories, emulsions, suspensions or solutions, the content of active compound being up to about 95%, advantageously between 10 and 75%.

In addition to solvents, gel-forming agents, suppository bases, tablet auxiliaries and other active compound carriers, suitable auxiliaries or excipients for the desired pharmaceutical formulation are also, for example, antioxidants, dispersants, emulsifiers, defoaming agents, flavor modifiers, preservatives, solubilizers or colorants.

The active compound can be administered orally, parenterally, intravenously or rectally, intranasal administration as an aerosol being preferred in particular in addition to oral administration.

For a form for oral use, the active compound is mixed with the additives suitable for this purpose such as excipients, stabilizers or inert diluents and brought into a suitable form for administration, such as tablets, coated tablets, hard gelatin capsules, and aqueous or oily solutions by the customary methods. Inert excipients which can be used are, for example, gum arabic, magnesia, magnesium carbonate, potassium phosphate, lactose, glucose or starch, in particular cornstarch. In this case, preparation can be carried out both as dry and as moist granules. Oily excipients or solvents which are suitable are, for example, vegetable or animal oils, such as sunflower oil or cod-liver oil.

For Pubcutaneous or intravenous administration, the active compound is brought into solution, suspension or emulsion with the substances suitable for this purpose, such as solubilizers, emulsifiers or other auxiliaries. Suitable solvents are, for example, physiological saline solution, alcohols, for example ethanol, propanol, glycerol, sugar solutions such as glucose or mannitol solutions or a mixture of solvents.

The following examples serve to illustrate the invention further.

EXAMPLE 1

Preparation of diethyl 2-formylbenzylphosphonate (A)

47.9 g (0.31 mol) of 2-chloromethylbenzaldehyde were heated to 160° C. together with 51.5 g (0.31 mol) of triethyl phosphite. Ethyl chloride distilled off during the course of this. The product was purified by fractional distillation.

Yield: 64.5 g (81%); b.p.: 130° C./0.3 mm;

1H-NMR (270 MHz, CDCl$_3$/TMS): $\delta = 1.23$ (t, 6H, P—O—CH$_2$CH$_2$—CH$_3$), 3.78 (d, 2H, CH$_2$—P) $J_{P-H} = 24$ Hz, 4.04 (dq,4H, P—O—CH$_2$—CH$_3$), 7.19–7.97 (m,4H,Ar—H)

EXAMPLE 2

Preparation of 2-formylbenzylphosphonic acid di(triethylammonium) salt (B) and monoethyl 2-formylbenzylphosphonate triethylammonium salt (C)

100 ml of 6 M HCl were added to 5.0 g (20 mmol) of diethyl 2-formylbenzylphosphonate and the mixture was boiled under reflux for 6 h. Water and HCl were distilled off in vacuo, and the residue was co-evaporated three times with toluene. The remaining brown material was chromatographed on silica gel (CH$_2$Cl$_2$/methanol/triethylamine: 75/24/1). Compounds B and C were obtained as oily products. It was possible to separate them by chromatography on diethylaminoethyl ®Sephadex A25 (Et$_3$NH$^+$ form, Pharmacia, Freiburg, West Germany). They differ in their elution behavior (Rf value). Elution was carried out with a triethylammonium bicarbonate gradient of from 0.3–1.0 m.

(B): Rf=0.1; yield: 2.4 g (30%); m.p.: 1H-NMR (270 MHz, DMSO/TMS): $\delta = 1.07$ (t,18H,N—CH$_2$—CH$_3$), 2.86 (q,12H,N—CH$_2$—CH$_3$), 3.23 (d,2H,CH$_2$—P) $J_{P-H} = 23$ Hz, 7.24–7.78 (m,4H,Ar—H), 10.31 (s,1H,CHO).

(C): Rf=0.3; yield: 1.4 g (21%);

1H-NMR (270 MHz, DMSO/TMS): $\delta = 1.01$–1.17 (m,12H, N—CH$_2$—CH$_3$ & P—O—CH$_2$—CH$_3$), 2.88 (q, 6H, N—CH$_2$—CH$_3$) 3.27 (d,2H,CH$_2$—P) $J_{P-H} = 23$ Hz, 3.68 ((dq,2H, P—O—CH$_2$—CH$_3$), 7.18–7.78 (m,4H,Ar—H), 10.31 (s,1H,CHO).

EXAMPLE 3

Preparation of 2-formylbenzylphosphonic acid di (triethylammonium) salt (B)

3.2 g (21 mmol) of trimethylsilyl bromide were added dropwise to 2.0 g (8 mmol) of the compound A in 10 ml of absolute dioxane, and the reaction mixture was heated to 50° C. and stirred at this temperature for 6 h. The mixture was evaporated, water was added several times and the solution was lyophilized. The crude product was purified by chromatography as in Example 2. Yield: 1.98 g (62%).

EXAMPLE 4

Diethyl 2-formylbenzylphosphonate thiosemicarbazone (D)

2.0 g (8 mmol) of the compound A and 0.73 g of thiosemicarbazide were dissolved or suspended in 200 ml of absolute ethanol. 2 ml of acetic acid were added and the mixture was boiled under reflux for 3 h. In the course of the slow cooling, the product D precipitated in crystalline form.

Yield: 1.8 g (68%); m.p.: 195 to 197° C.;

$^1$H-NMR (270 MHz, CDCl$_3$/TMS): $\delta = 1.16$ (t,6H,CH$_2$—CH$_3$)3.38 (d,2H, CH$_2$—P, $J_{P-H}=23$ Hz), 3.94 (dq,4H, CH$_2$—CH$_3$), 7.23–7.39 (m,3H,Ar—H), 8.40 (s,1H,Ar—H), 11.37 (s,1H,Ar—CH=N).

EXAMPLE 5

Diethyl 2-formylbenzylphosphonate nicotinic acid hydrazone (E)

2.0 g (8 mmol) of the compound A and 1.07 g (8 mmol) of nicotinic acid hydrazide were dissolved in 30 ml of absolute ethanol. After adding 1 ml of acetic acid, the mixture was boiled under reflux for 8 h. The solvent was removed by rotary evaporation and the residue was chromatographed on silica gel (eluent CH$_2$Cl$_2$/EtOH 9.5/0.5; Rf =0.45). The product E was obtained in crystalline form. Yield: 2.2 g (73%); m.p.: 136° to 140° C.;

$^1$H-NMR$^{270}$ MHz, CDCl$_3$/TMS): $\delta=1.14$–1.37 (m,6H,CH$_3$), 3.61–3.79 (d,2H,CH$_2$—P), $J_{P-H}=24$ Hz, 3.87–4.16 (m,4H,CH$_2$—CH$_3$), 7.11–7.49 (m,4H,Ar—H), 7.70–9.23 (m,5H,Py-H), 10.17 & 11.25 (each s, ratio 1:3, 1H,NH).

EXAMPLE 6

Diethyl 2-(3,4-dimethyl-5-phenyloxazolidin-2-yl)benzylphosphonate (F)

2.0 g (8 mmol) of the compound A and 1.32 g (8 mmol) of (-)-ephedrine were dissolved in 100 ml of benzene and heated under reflux in a water separator for 24 h. The solvent was then removed by rotary evaporation and the residue was chromatographed on silica gel (eluent CH$_2$Cl$_2$/ethanol 9.5/0.5; Rf=0.55). The product F was obtained as an oil.

Yield: 2.4 g (75%);

$^1$H-NMR (270 MHz, CDCl$_3$/TMS); $\delta=0.80$, (d,3H,CH—CH$_3$), 1.25 (m,6H,O—CH$_2$—CH$_3$), 2.27 (s,3H,N—CH$_3$), 3.18 (dq,1H,CH—CH$_3$), 3.20 & 3.28 (dd,1H,Ph—CH—CH); 3.59–3.76 (m,2H,CH$_2$—P); 4.01 (m,4H,O—CH$_2$—CH$_3$), 5.19 (s,1H,Ar—CH-(O—)(N—), 7.16–7.45 (m,8H,Ar—H), 7.89–7.98 (m,1H,Ar—H).

EXAMPLE 7

Pathogen-free NMRI mice having a weight of about 15 g were infected intraperitoneally with Herpes simplex Type 1 and then treated intraperitoneally, orally or subcutaneously with the compounds mentioned in Table 1. The treatment was carried out twice daily over the course of 2.5 days, starting after infection. The result of treatment was determined on the basis of the course of the disease and the survival rate compared to the untreated infection controls. The controls received a water-soluble methylhydroxyethylcellulose (viscosity 300 pa.s, administered in 2% strength solution) instead of the compounds to be tested. The experiments were carried out using groups of 5 mice each per preparation.

The chemotherapeutic action of the compound A can be seen from Table 1.

TABLE 1

|  | | Herpes simplex 1 | |
|---|---|---|---|
| Preparation | Dosage (mg/kg) | Surviving animals | Average survival time (days) |
| Control | sc 0 | 1 | 6.7 |
| A | sc 2.5 | 2 | 9.0 |
| A | sc 25 | 0 | 7.2 |
| A | sc 250 | 0 | 8.4 |
| Control | po 0 | 1 | 8.0 |
| A | po 2.5 | 4 | 8.0 |
| A | po 25 | 5 | — |
| A | po 250 | 4 | 8.0 |
| Control | sc 0 | 1 | 8.3 |
| C | sc 3 | 1 | 8.5 |
| C | sc 10 | 3 | 8.0 |
| C | sc 30 | 4 | 10.0 |
| Control | po 0 | 1 | 7.8 |
| C | po 3 | 4 | 9.0 |
| C | po 10 | 3 | 8.0 |
| C | po 30 | 1 | 8.3 |
| Control | sc 0 | 1 | 8.3 |
| B | sc 3 | 2 | 7.8 |
| B | sc 10 | 3 | 7.0 |
| B | sc 30 | 3 | 6.5 |
| Control | po 0 | 1 | 7.8 |
| B | po 3 | 3 | 7.0 |
| B | po 10 | 2 | 8.3 |
| B | po 30 | 3 | 6.0 |
| Control | ip 0 | 1 | 8.3 |
| A | ip 3 | 0 | 8.0 |
| A | ip 10 | 4 | 9.0 |
| A | ip 30 | 3 | 8.5 | po = orally
sc = subcutaneously
ip = intraperitoneally

EXAMPLE 8

Cell cultures of Hela and Vero cells were inoculated into microtitre plates and infected with myxoviruses (influenza A2). 2 Hours after infection, the compounds B and C were added to the infected cell cultures in various dilutions. 48 to 72 hours after infection, the result of treatment was determined microscopically and photometrically by neutral red absorption (color test according to Finter) (Finter, N. B. Interferons, 1966) on the basis of the cytopathogenic effect. The minimum concentration at which about half the infected cells do not show a cytopathogenic effect is regarded as the minimum inhibitory concentration (MIC). The results are summarized in Table 2.

TABLE 2

|  | Influenza A2 | |
|---|---|---|
| Substance | MIC (µg/ml) | MTD (µg/ml) |
| C | 44.4 | >400 |
| B | 4.94 | >400 |

MIC = minimum inhibitory concentration
MTD = maximum tolerated dose

EXAMPLE 9

Pathogen-free NMRI mice having a weight of about 16 g were infected intranasally with influenza A2 and then treated subcutaneously and orally with the compounds mentioned in Table 3. The compounds were administered to the animals under slight ether anesthesia using one drop of virus suspension in each of the nostrils. The treatment was carried out twice daily over the course of 2.5 days, starting after infection. Amantadine was always used as the comparison. The success of the treatment was determined on the basis of the course of the disease and the survival rate compared to the untreated infection controls. The controls received a water-soluble methylhydroxyethylcellulose (viscosity 300 Pa.s, administered in 2% strength solution) instead of the compounds to be tested. The experiments were carried out using groups of 5 mice each per preparation. The chemotherapeutic action is shown in Table 3.

TABLE 3

| Preparation | Dosage (mg/kg) | | Number of surviving animals | Average survival time (days) |
|---|---|---|---|---|
| Control | po | 0 | 2 | 7.5 |
| Amantadine | po | 80 | 5 | — |
| A | po | 2.5 | 4 | 9.0 |
| A | po | 3 | 4 | 8.0 |
| A | po | 10 | 4 | 7.0 |
| A | po | 25 | 2 | 6.3 |
| A | po | 30 | 2 | 7.3 |
| Control | sc | 0 | 0 | 6.6 |
| Amantadine | sc | 80 | 5 | — |
| A | sc | 2.5 | 2 | 6.7 |
| A | sc | 25 | 3 | 7.0 |
| Control | sc | 0 | 2 | 6.7 |
| Amantadine | sc | 80 | 5 | — |
| B | sc | 1.5 | 1 | 8.5 |
| B | sc | 15 | 4 | 8.0 |
| Control | po | 0 | 1 | 6.5 |
| Amantadine | po | 80 | 4 | 8.0 |
| B | po | 1.5 | 3 | 8.5 |
| B | po | 15 | 5 | — |
| B | po | 150 | 3 | 7.0 |
| Control | sc | 0 | 0 | 6.8 |
| C | sc | 0.25 | 5 | — |
| C | sc | 2.5 | 5 | — |
| C | sc | 25 | 3 | 7.5 |
| Control | po | 0 | 0 | 7.2 |
| C | po | 0.25 | 5 | — |
| C | po | 2.5 | 2 | 6.0 |
| C | po | 25 | 5 | — |
| Control | po | 0 | 0 | 6.6 |
| D | po | 0.25 | 4 | 8.0 |
| D | po | 2.5 | 1 | 7.0 |
| D | po | 25 | 2 | 7.3 |
| Control | po | 0 | 0 | 6.6 |
| E | po | 0.25 | 4 | 8.0 |
| E | po | 2.5 | 3 | 6.7 |
| E | po | 25 | 3 | 6.0 |
| Control | po | 0 | 1 | 7.0 |
| F | po | 0.25 | 3 | 6.5 |
| F | po | 2.5 | 3 | 6.5 |
| F | po | 25 | 2 | 7.0 | sc = subcutaneously
po = orally

EXAMPLE 10

Laboratory mice (NMRI, female, weight 20–24 g) were infected intravenously with Friend leukemia virus (FLV)-containing mouse serum. The treatment was started 40 h after infection. The mice were treated over the course of 10 days with the substances indicated in Table 4. The substances indicated were administered orally or intraperitoneally once a day. 14 days after infection, the animals were sacrificed by dislocation and the spleens were removed. The weight of the spleens was determined. As a measurement parameter of the therapeutic activity, the weight of the spleen of the animals which had been treated with compounds A and D was related to that of the untreated infection control.

Suramin and azidothymidine (AZT) were used as standard substances. The action of the preparations is shown in Table 4.

TABLE 4

| | Friend leukemia virus | | |
|---|---|---|---|
| Preparation | Dosage | Survival rate % | Relative weight of the spleen % of body weight |
| Control | po 0 | 100 | 12.36 |
| AZT | po 15.5 | 100 | 3.26 |
| A | po 17.5 | 100 | 7.74 |
| A | po 81 | 100 | 5.67 |
| Control | ip 0 | 100 | 10.64 |
| AZT | ip 50.0 | 100 | 7.60 |
| D | ip 50.0 | 100 | 7.60 |
| Control | ip 0 | 100 | 12.36 |
| Suramin | ip 50 | 70 | 6.06 |
| A | ip 25 | 90 | 6.27 |
| A | ip 50 | 100 | 6.52 | ip = intraperitoneally
po = orally

We claim:
1. A compound of the formula (I)

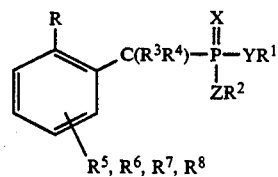

in which R is an aldehyde or a group, which can be converted into an aldehyde, of the formula Ib, Ic or Id

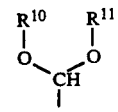  Ib

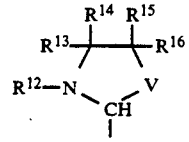  Ic

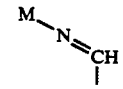  Id in which $R^{10}$ and $R^{11}$, which may be identical or different, are a straight-chain or branched alkyl group having 1 to 10 carbon atoms or $R^{10}$ and $R^{11}$ together form a cyclic acetal having 2 or 3 carbon atoms int he ring, $R^{12}$ to $R^{16}$, which may be identical or different, are a
  straight-chain or branched alkyl group having 1 to
  10 carbon atoms or an aryl group having 6, 10 or 14
  carbon atoms, V is oxygen or sulfur, M is a hydroxyl group, a straight-chain or branched
  alkyl group having 1 to 10 carbon atoms, an aralkyl
  group having 7 to 20 carbon atoms, an aryl group
  having 6, 10 or 14 carbon atoms or a radical of the
  formula Ie or If

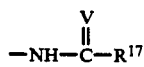

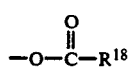

in which $R^{17}$ is a straight-chain or branched alkyl group having 1 to 10 carbon atoms, an amino, pyridine, or aryl group having 6, 10 or 14 carbon atoms and $R^{18}$ is an amino group, a pyridine group, a straight-chain or branched alkyl group having 1 to 10 carbon atoms, an aryl group having 6, 10 or 14 carbon atoms or an aralkyl group having 7 to 20 carbon atoms, $R^1$ and $R^2$, which are the same or different from each other, are an alkyl group having 1 to 10 carbon atoms, an alkenyl or alkynyl group having 2 to 10 carbon atoms, hydrogen, an aralkyl group having 7 to 16 carbon atoms, sodium, potassium, calcium, magnesium, aluminum, lithium, ammonium, or triethylammonium, $R^3$ and $R^4$ are an alkyl group having 1 to 4 carbon atoms, an alkenyl or alkynyl group having 2 to 4 carbon atoms, or hydrogen, $R^5$, $R^6$, $R^7$, and $R^8$ are chlorine, broine, methoxy or hydrogen and X, Y and Z are oxygen.

2. Diethyl 2-formylbenzylphosphonate.

3. 2-Formylbenzylphosphonic acid di(triethylammonium) salt.

4. Monoethyl 2-formylbenzylphosphonate triethylammonium salt.

5. Diethyl 2-formylbenzylphosphonate thiosemicarbazone.

6. Diethyl 2-formylbenzylphosphonate nicotinic acid hydrazone.

7. Diethyl 2-(3,4-dimethyl-5-phenyloxazolidin-2-yl)-benzylphosphonate.

8. A pharmaceutical preparation containing an effective amount of the compound of formula I as claimed in claim 1 combined with an acceptable pharmaceutical excipient.

* * * * *

UNITED STATES PATENT AND TRADEMARK OFFICE
CERTIFICATE OF CORRECTION

PATENT NO. : 5,278,152
DATED : January 11, 1994
INVENTOR(S) : Anuschirwan Peyman et al.

It is certified that error appears in the above-indentified patent and that said Letters Patent is hereby corrected as shown below:

Claim 1, column 12, line 58, change "int he" to --in the--.

Claim 1, column 14, line 6, change "broine" to --bromine--.

Signed and Sealed this

Sixteenth Day of August, 1994

Attest:

BRUCE LEHMAN

*Attesting Officer*     *Commissioner of Patents and Trademarks*